(12) United States Patent
Durgan et al.

(10) Patent No.: US 8,995,611 B2
(45) Date of Patent: Mar. 31, 2015

(54) SCAN START AND/OR END POSITION IDENTIFIER

(75) Inventors: Jacob Durgan, Mayfield Village, OH (US); Nabi Abraham Cohn, Chardon, OH (US); John Cressman, Chardon, OH (US); James Thomas Richards, Euclid, OH (US); Shlomo Gotman, Haifa (IL)

(73) Assignee: Koninklijke Philips N.V., Eindhoven (NL)

( * ) Notice: Subject to any disclaimer, the term of this patent is extended or adjusted under 35 U.S.C. 154(b) by 166 days.

(21) Appl. No.: 13/816,576

(22) PCT Filed: Aug. 10, 2011

(86) PCT No.: PCT/IB2011/053570
§ 371 (c)(1),
(2), (4) Date: Feb. 12, 2013

(87) PCT Pub. No.: WO2012/023088
PCT Pub. Date: Feb. 23, 2012

(65) Prior Publication Data
US 2013/0148778 A1    Jun. 13, 2013

Related U.S. Application Data

(60) Provisional application No. 61/374,009, filed on Aug. 16, 2010.

(51) Int. Cl.
*A61B 6/04* (2006.01)
*A61B 6/03* (2006.01)
(Continued)

(52) U.S. Cl.
CPC .............. *A61B 6/0492* (2013.01); *A61B 6/032* (2013.01); *A61B 6/0407* (2013.01);
(Continued)

(58) Field of Classification Search
CPC ........ A61B 6/0492; A61B 6/04; A61B 6/032; A61B 6/0407; A61B 6/0457; A61B 6/08; A61B 6/545; A61B 6/4423; A61B 6/548
USPC .................................. 378/4, 20, 19, 62, 204
See application file for complete search history.

(56) References Cited

U.S. PATENT DOCUMENTS

| 6,460,206 | B1 | 10/2002 | Blasche et al. |
| 7,308,075 | B2 | 12/2007 | Barkow et al. |
| 7,633,501 | B2 * | 12/2009 | Wood et al. ................... 345/419 |

(Continued)

FOREIGN PATENT DOCUMENTS

WO    2006126108 A1    11/2006

*Primary Examiner* — Irakli Kiknadze (57) ABSTRACT

A subject support (118) for an imaging system (100) includes a moveable portion (122) that includes a surface (204) on which the subject is loaded and that is configured to move into an examination region of the imaging system where the subject is to be scanned. The support further includes a scan position identifier (126) that generates a signal indicative of at least one of a start scan position or an end scan position for a predetermined region of interest of the subject based on a location of the region of interest on the moveable portion of the subject support for an arbitrary relative position of the moveable portion with respect to the examination region.

18 Claims, 8 Drawing Sheets

(51) Int. Cl.
  *A61B 6/08* (2006.01)
  *A61B 6/00* (2006.01)

(52) U.S. Cl.
  CPC ................ *A61B 6/0457* (2013.01); *A61B 6/08* (2013.01); *A61B 6/545* (2013.01); *A61B 6/547* (2013.01); *A61B 6/04* (2013.01); *A61B 6/4423* (2013.01); *A61B 6/548* (2013.01)
  USPC .............................. 378/20; 378/208; 378/205

(56) References Cited

U.S. PATENT DOCUMENTS

| | | |
|---|---|---|
| 7,639,782 B2 * | 12/2009 | Zelnik et al. .................... 378/62 |
| 2002/0118280 A1 | 8/2002 | Medlar et al. |
| 2004/0081341 A1 | 4/2004 | Cherek et al. |
| 2006/0034421 A1 | 2/2006 | Barkow et al. |
| 2008/0016620 A1 | 1/2008 | Haras |
| 2008/0194942 A1 | 8/2008 | Cumpson et al. |

* cited by examiner

SCAN START AND/OR END POSITION IDENTIFIER

CROSS REFERENCE TO RELATED APPLICATIONS

This application is a national filing of PCT application Ser. No. PCT/IB2011/053570, filed Aug. 10, 2011, published as WO 2012/023088 A1 on Feb. 23, 2012, which claims the benefit of U.S. provisional application Ser. No. 61/374,009 filed Aug. 16, 2010, which is incorporated herein by reference.

The following generally relates to imaging an object or subject and more particularly to identifying at least one of a start scan position or an end scan position for an object or subject to be scanned.

Medical imaging has been used to target particular tissue of interest such as the heart, lungs, brain, arm, leg, torso, whole body, tumor, etc. Imaging systems such as a CT scanner generally are stationary, and the subject (or object) to be scanned is moved into and out of an examination region of the imaging system via a subject support so that a defined longitudinal volume of the subject covering the tissue of interest to be scanned passes through the examination region and is scanned. The volume generally is specified by a start position, with respect to the horizontal subject support motion, and a length or end position with respect to the start position. The start position has been determined based on a pre-scan (a surview, scout, or pilot).

For the pre-scan, the subject is loaded on the subject support. With one technique, the technologist moves the subject support into the examination region, and a laser fixidly attached to the scanner provides a visual indication of iso-center of the examination region for the technologist. The technologist positions the subject support in the examination region so that a scan start position for a region of interest of the subject to be scanned is defined with respect to isocenter using the fixed laser. With another technique, the scan start position is set with respect to an external laser, and the subject support is automatically moved a pre-programmed distance from the external laser to isocenter. The technologist can initiate the pre-scan to begin scanning at the scan start position.

With another technique, the technologist positions the subject in the examination region with respect to isocenter and the horizontal position of the subject support is set to zero to mark a reference position. The technologist can then freely move the subject support away from this position to facilitate preparing the subject for the scan. The technologist can then enter a starting position of zero at the console to initiate the pre-scan, and the subject support is automatically moved to the zero position for the pre-scan. Unfortunately, the foregoing techniques all require moving the subject support to a fixed scan start marking position to define the start position relative to the examination region, which requires extra steps that consume time that could otherwise be utilized with the subject, for the procedure, and/or to improve throughput.

Once the scan start position is defined, a length or scan end position typically is defined. With one technique, a default scan length is automatically selected based on the selected scan protocol. Unfortunately, a default setting may not be optimal or well suited for each subject and, as a consequence, may lead to unnecessary patient dose. With another technique, the technologist sets the length based on their knowledge of the required scan length or patient size. Typically, this length will be a considerable overestimation of the necessary length since if the scan were not long enough it may require rescanning the subject to acquire the necessary length for planning Unfortunately, over scanning and re-scanning increase patient dose.

With another technique, a scan length is not set, and the technician starts the scan and simply stops the scan via controls at the console when they believe that enough of the patient has been covered to plan a diagnostic scan. However, this approach requires the technologist to pay close attention while the scan is being displayed line by line in real-time, and depends on their quick reaction to stop the scan at an appropriate time. Even so, there may still be some delay from the time a position on the patient is actually imaged until the time that the corresponding line is displayed on the console screen. Further time may be required for the technologist's reaction, and then for the system to respond to the stop request. Any additional scan length consumes extra time and may cause unnecessary patient dose.

Aspects of the present application address the above-referenced matters and others.

According to one aspect, a subject support for an imaging system includes a moveable portion that includes a surface on which the subject is loaded and that is configured to move into an examination region of the imaging system where the subject is to be scanned. The support further includes a scan position identifier that generates a signal indicative of at least one of a start scan position or an end scan position for a predetermined region of interest of the subject based on a location of the region of interest on the moveable portion of the subject support for an arbitrary relative position of the moveable portion with respect to the examination region.

According to another aspect, a method includes generating a first signal indicative of one of a start scan position or an end scan position by aligning a first scan marker with a first region of interest of a subject loaded on a moveable portion of a subject support independent of a location of the moveable portion with respect to an examination region in which the region of interest is scanned and creating a scan plan with at least one of a scan start or end position based on the signal.

According to another aspect, an imaging system includes a stationary gantry and a rotating gantry. The rotating gantry includes a radiation source that emits radiation and a radiation sensitive detector array located opposite the source across an examination region. A subject support supports a subject for scanning and is configured to move the subject into and out of the examination region. A scan position identifier identifies at least a start scan position for the subject solely based on a location of subject on the subject support.

The invention may take form in various components and arrangements of components, and in various steps and arrangements of steps. The drawings are only for purposes of illustrating the preferred embodiments and are not to be construed as limiting the invention.

FIG. 1 illustrates an imaging system 100 such as a computed tomography (CT) scanner. In other embodiments, the imaging system 100 additionally or alternatively includes one or more other imaging modalities. The illustrated imaging system 100 includes a stationary gantry 102 and a rotating gantry 104. The rotating gantry 104 is rotatably supported by the stationary gantry 102 and rotates around an examination region 106 about a longitudinal or z-axis 108. A radiation source 110, such as an x-ray tube, is supported by the rotating gantry 104. The radiation source 110 emits radiation that traverses the examination region 106 and an object or subject therein. A source collimator collimates the radiation to form a generally cone, wedge, fan or other shaped radiation beam. A radiation sensitive detector array 112 subtends an angular arc opposite the radiation source 110 across the examination region 106. The detector array 112 includes one or more rows of detectors. The detector array 112 detects radiation traversing the examination region 106 and generates projection data indicative thereof. A reconstructor 114 reconstructs the projection data and generates volumetric image data indicative thereof.

Figure 1A:
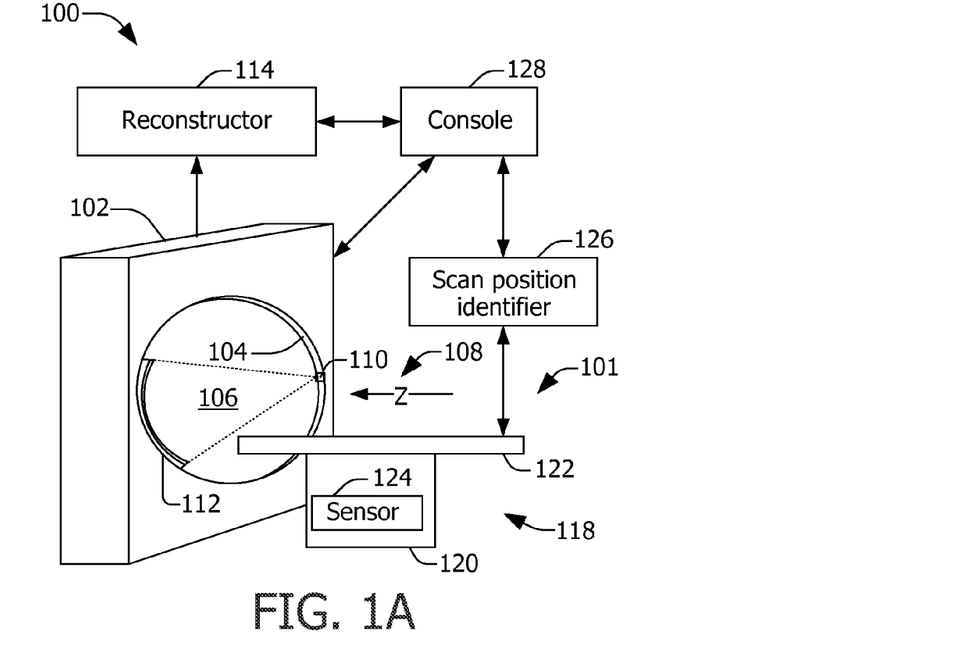
FIG. 1 illustrates an example imaging system in connection with a scan position identifier that facilitates identifying at least one of a scan start position, a scan end position, or a scan extent (length).
Figure 1B:
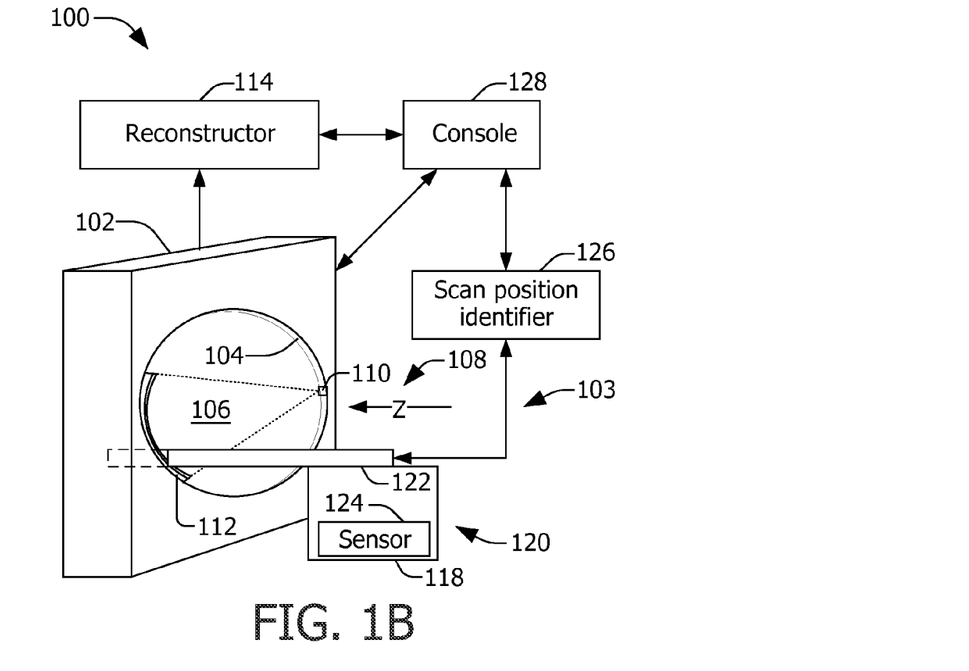

A subject support 118 supports an object or subject such as a human or animal patient for scanning The illustrated subject support 118 includes a stationary portion 120 and a moveable portion 122, which is moveable relative to the stationary portion 120. The moveable portion 122 is configured for at least horizontal motion into and out of the examination region 106. FIG. 1A shows the moveable portion 122 in a (retracted) position 101 in which the moveable portion 122 is not located in the examination region 106, and FIG. 1B shows the moveable portion 122 in a (extended) position 103 in which a portion of the moveable portion 122 is located in the examination region 106. A position sensor 124 provides a signal indicative of a horizontal location of the moveable portion 122 with respect to the examination zone 106.

A scan position identifier 126 facilitates identifying at least one of a scan start position or a scan end position for a pre-scan and/or a diagnostic scan. As described in greater detail below, in one instance, the scan position identifier 126 can be used to identify the scan start and/or end position based on a location of the subject on the subject support. In one instance, this includes identifying the scan start and/or end position without having to move the subject support to any fixed scan start marking position and/or without reference to and/or independent of location of the moveable portion 122 with respect to the examination region 106. This mitigates having to have the technologist perform extra non-imaging based steps for defining the scan start and/or end position and thus may simplify patient study preparation workflow, reduce the amount of time a patient has to be on the subject support 118 and in the exam room, etc., and may optimize or improve the accuracy at which the scanned volume coincides with the volume necessary for scanning the tissue of interest and reduce dose relative to a configuration in which the scan position identifier 126 is not used or is omitted.

A general-purpose computing system or computer serves as an operator console 128. The console 128 includes various input and output devices such as a keyboard, a mouse, a display, etc. The console includes one or more processors that executes computer readable instructions embedded or encoded on computer readable storage medium (non-transitory physical memory) which allows an operator to control operation of the system 100 such as initiating a pre-scan and/or diagnostics scan based on a start and/or end scan position determined via the scan position identifier 126, stop scanning, set protocol parameters, etc.

Figure 2A:
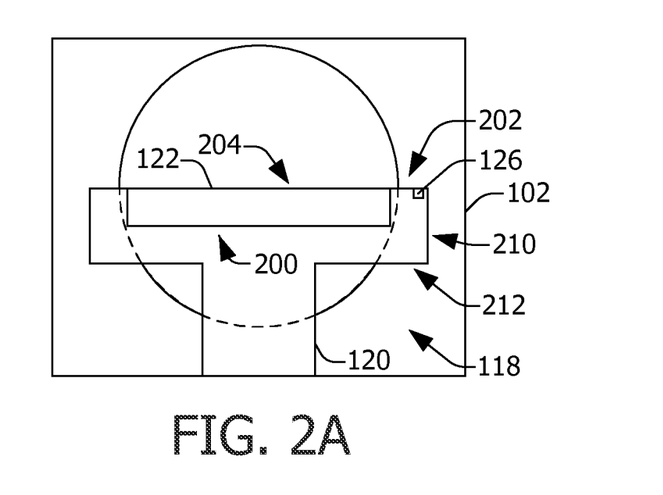
FIGS. 2-9 show various non-limiting embodiments of the scan position identifier in connection with the example imaging system of FIG. 1.
Figure 2B:
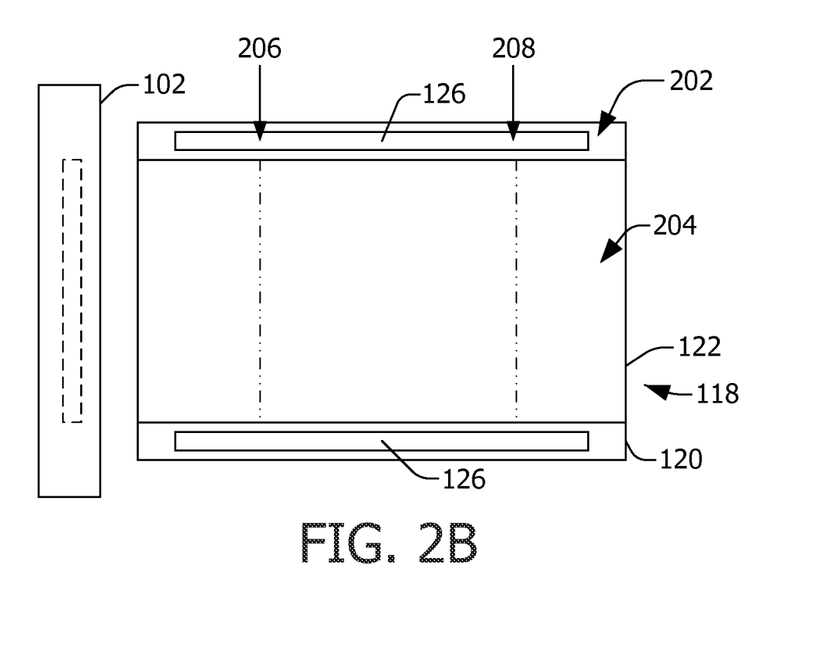

FIG. 2 illustrates an example embodiment of the scan position identifier 126. For this embodiment, the moveable portion 122 of the subject support 118 is located within a recess 200 of the stationary portion 120 and the scan position identifier 126 is located on a side 202 of the stationary portion 120 which is generally parallel and adjacent to a side 204 of the moveable portion 122 on which a subject would be positioned for scanning Such positioning allows for easy access and visibility for the technologist. As shown in FIG. 2B, the scan position identifier 126 can run along a predetermined length of the side 202. In this embodiment, the length is less than the entire length of the side. In other embodiments, the length of the scan position identifier 126 with respect to the side 202 can be longer or shorter.

In FIG. 2, the scan position identifier 126 includes an interaction-sensitive component, which is configured to generate a signal in response to interaction with the scan position identifier 126. Non-limiting examples of interactions include, but are not limited to, pressure or physical contact such as a finger or other object pressing on the scan position identifier 126, thermal such as heat transferred between a finger touching the scan position identifier 126 and the scan position identifier 126, non-contact such as propagating waves induced by a finger approaching the scan position identifier 126, electrical characteristics (e.g., capacitive, inductive, resistive, current, voltage, etc.) between the finger and the scan position identifier 126, optical signals, etc. between the finger and the scan position identifier 126, audible (e.g., voice recognition), and/or other interaction.

By way of non-limiting example and as shown in FIG. 2B, after a subject (not shown for explanatory purposes) has been loaded on the moveable portion 122, a technician may approach the subject support 118 and touch a first region 206 of the scan position identifier 126 to identify a start scan position and, optionally, touch a second region 208 of the scan position identifier 126 to identify an end scan position. Upon touching the first position 206 on the scan position identifier 126, a first signal indicative of the relative location of the first position 206 with respect to the moveable portion 122 is generated. Likewise, where the second region is touched, a second signal indicative of the relative location of the second position 208 with respect to the moveable portion 122 is generated. In both instance, the moveable portion 122 may be located at an arbitrary position with respect to the stationary gantry 102 and hence the examination region 106.

These generated signals are conveyed to the console 128 (FIG. 1) and/or other computing system, which can incorporate the information in connection with an executing scan planning application to set start and/or end scan positions for a pre-scan and/or a diagnostic scan. The technologist can accept these positions, for example, by providing an input indicative of accepting the positions at the console, simply initiating scanning, and/or otherwise. The technologist can also reject one or more of the positions and/or manually enter one or more of the positions via the console 128 or through the scan position identifier 126, or manually enter an extent in lieu of the end position via the console 128 or otherwise. Where the technologist only identifies the scan start position via the scan position identifier 126, the technologist can manually enter the end position or scan extent/length via the console 128.

Various techniques can be employed for identifying, changing, and/or cancelling an identified position. For example, in one embodiment identifying a position may entail multiple touches such as two touches at the same location (e.g., the region 206), one touch at the region 206 and another touch at another location such as a validation region, etc. In another embodiment, the technologist identifies a position by pressing on the region 206 for a predetermined period of time. In another embodiment, the technologist identifies a position by pushing a button, actuating a switch, etc. In another embodiment, the technologist identifies a position by providing a voice command (e.g., "start position") while pressing on the region 206. In another embodiment, the technologist can touch and slide the region 206 to another location on the scan position identifier 126 to move the identified region. In another embodiment, a subsequent interaction (e.g., subsequent touching) with the region 206 deselects or cancels the identified region 206. The above examples provide non-limiting approaches, and other approaches are also contemplated herein.

Various approaches can be used to apprise the technologist of the identified region(s) such as visual, audible, tactile, and/or other feedback through the subject support 118, the stationary gantry 102, the console 128, and/or other component of the system 100 and/or a component external to the system 100. For example, in one instance, a lighting device(s) (e.g., a light emitting diode (LED)) is provided to light an identified region. In the illustrated embodiment, this may include lighting the region 206 and 208 on the scan position identifier 126. The lighting device can be internal and/or external to the scan position identifier 126. In another instance, a mechanical component such as a bead, a switch, a lever, etc. is employed to mark the identified region(s). In this instance, moving the bead, switch, lever, etc. may identify the region and concurrently provide a visual marker to the technician via its location, state (open or closed), etc.

It is to be appreciated that the scan position identifier 126 can additionally or alternatively be located on other sides of the stationary portion 120 such as on a side 210 which is perpendicular to the side 204 and faces outward from the subject support 118, a side 212 which is parallel to the side 204 but faces in an opposite direction, and/or other side. Having the scan position identifier 126 farther away from and/or at harder to reach regions may mitigate accidental contact (e.g., by the technologist, the patient, equipment, etc.) and/or intentional disrupting contact (e.g., a disorderly patient, a child, etc.). In the illustrated embodiment, the scan position identifier 126 is located on both sides of the subject support 118. In another embodiment, the scan position identifier 126 is only located on one of the sides. In another embodiment, the start position is identified on one of the sides and the end position is located on the other of the sides.

Various approaches can be used to implement the scan position identifier 126. Examples include, but are not limited to, electrical (capacitive, inductive, resistive, etc.), magnetic, optical, radio frequency, transducive, etc.

Figure 3:
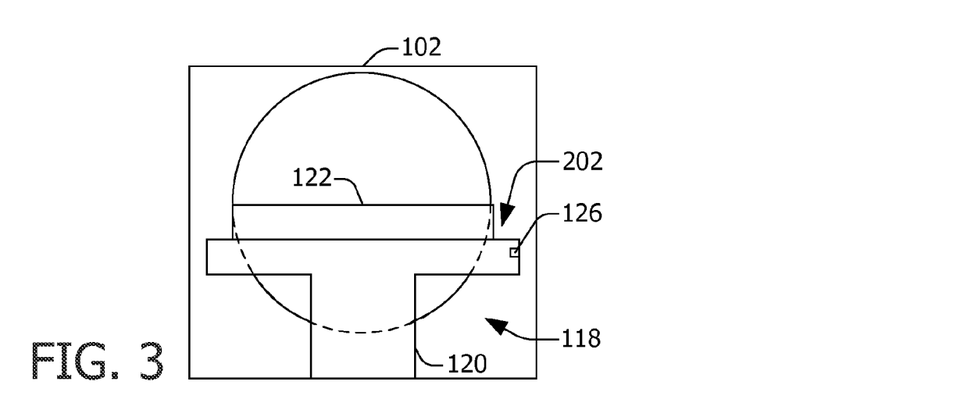

FIG. 3 illustrates an embodiment in which the moveable portion 122 of the subject support 118 sits at least partially above the stationary portion 120 and the scan position identifier 126 is located on the side 202 of the stationary portion 120.

Figure 4:
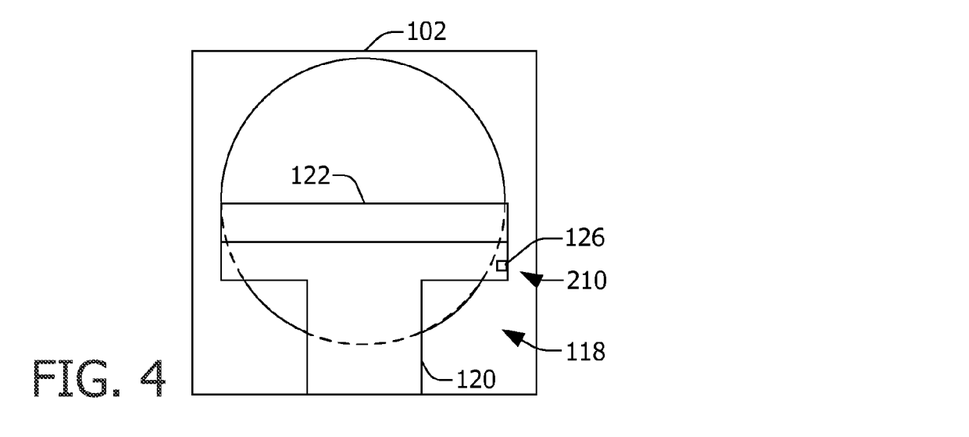

FIG. 4 illustrates an embodiment in which the moveable portion 122 of the subject support 118 sits at least partially above the stationary portion 120 and the scan position identifier 126 is located on the side 210 of the stationary portion 120.

Figure 5:
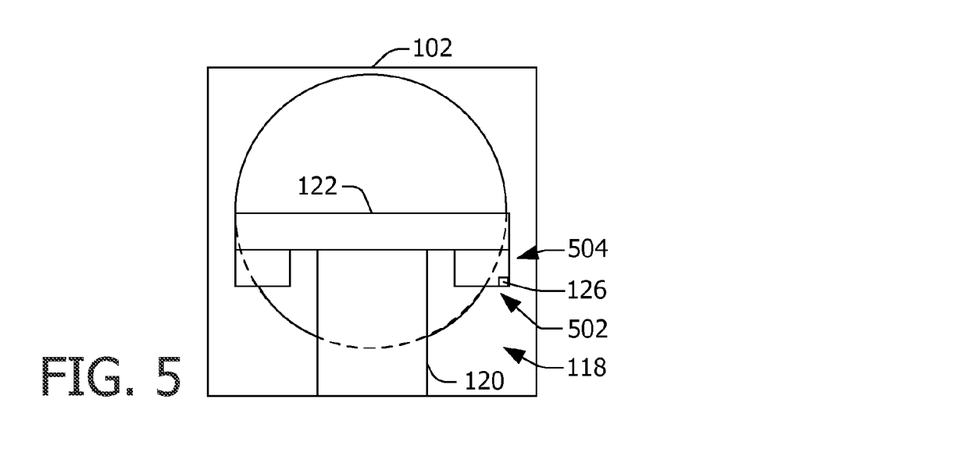

FIG. 5 illustrates an embodiment in which the moveable portion 122 of the subject support 118 sits at least partially above the stationary portion 120, and the scan position identifier 126 is located at least partially on an underside 502 of the moveable portion 122 and at least partially on a side 504 of the moveable portion 122. In this instance, since the scan position identifier 126 is located on the moveable portion 122, at least part of the scan position identifier 126 will be located in the examination region 106 during scanning As such, the scan position identifier 126 can be made of a material that minimizes any interaction between the scan position identifier 126 and the radiation beam which may show up in the reconstructed image.

With respect to the example embodiments shown in FIGS. 2-5, the scan position identifier 126 may be at least partially enclosed in a material such as a membrane, container, or the like. Using a sealed or particulate impermeable material or the like may allow for protecting the scan position identifier 126 from particulate such as bodily fluids, dust, or so forth, and/or render the scan position identifier 126 easily cleanable, sterilizeable, disinfectable, etc.

Figure 6A:
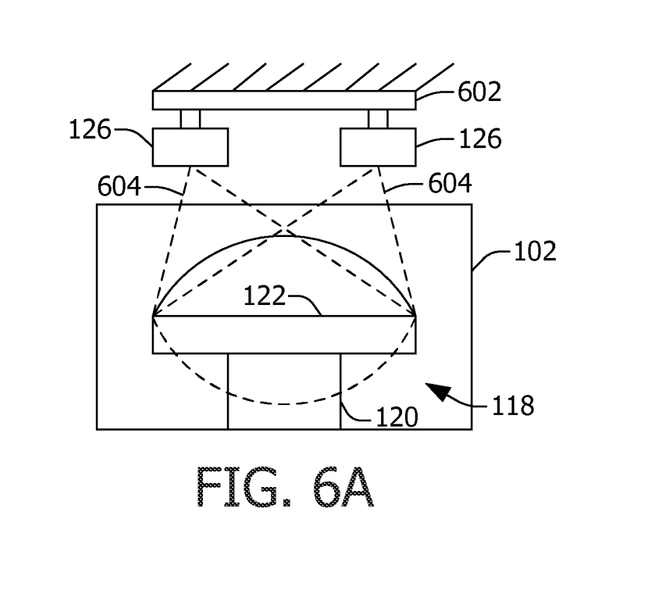
Figure 6B:
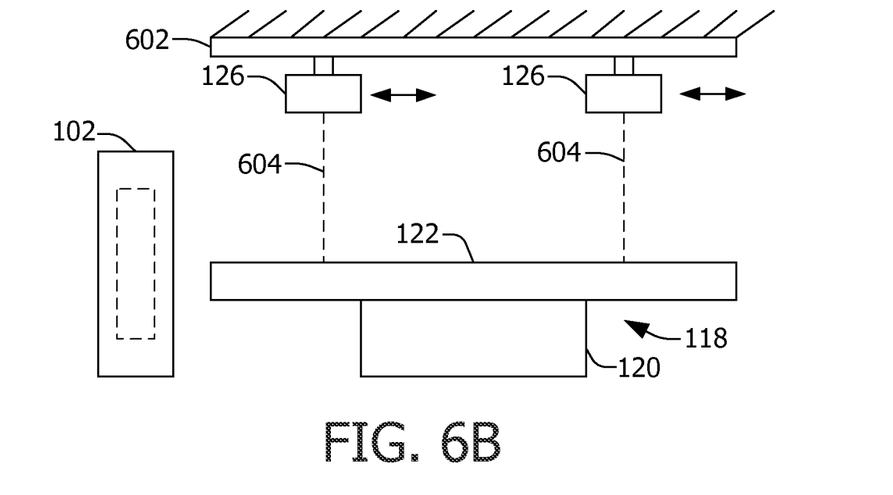

FIG. 6 illustrates an embodiment in which the scan position identifier 126 is located external to the system 100. More particularly, the illustrated scan position identifier 126 is slidably affixed to a tract 602 that is fixidly mounted, for example, to a ceiling or other structure in an exam room. The scan position identifier 126 is configured for movement back and forth on the tract 602 as shown in FIG. 6(B). In the illustrated embodiment, the scan position identifier 126 includes a lighting device(s) that emits a light beam 604 that illuminates a portion of the surface 204 of the moveable portion 122 of the subject support 118.

In operation, the technologist manually moves and aligns the light beam 604 with respect to the subject (not shown) on the subject support 118 to identify at least one of the start scan position 206 and optionally the end scan position 208. Similar to above, various approaches can be used to accept, change, cancel, etc. an identified position. For example, merely sliding the scan position identifier 126 may activate the scan position identifier 126 and then leaving the scan position identifier 126 at the position for some period of time may accept the identified region. Subsequent moving of the scan position identifier 126 may or may not change or cancel the identified position.

In other embodiments, the scan position identifier 126 may include one or more components (e.g., buttons, switches, sensors, levers, etc.) for activating the beam 604, accepting an identified position, changing a position, cancelling a position, etc. In another embodiment, a fixed light emitting object can be moved, or alternatively, the angle of projection of the light can be moved to find a start and/or stop position based on a calculated distance from the angle of projection.

In other embodiments, a remote control includes controls for controlling the scan position identifier 126, such as moving the scan position identifier 126 along the tracts 602, stopping the scan position identifier 126 at a particular position, turning the beam 604 on and off, etc. The remote control may be configured to communicate with the scan position identifier 126 via wire and/or wireless communications, directly and/or through another apparatus (e.g., the console 128, the gantry 102, etc.).

Figure 7A:
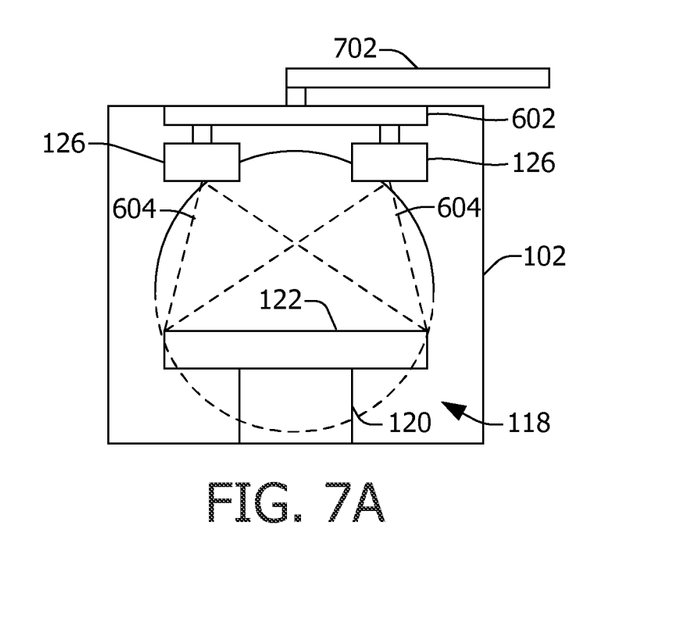
Figure 7B:
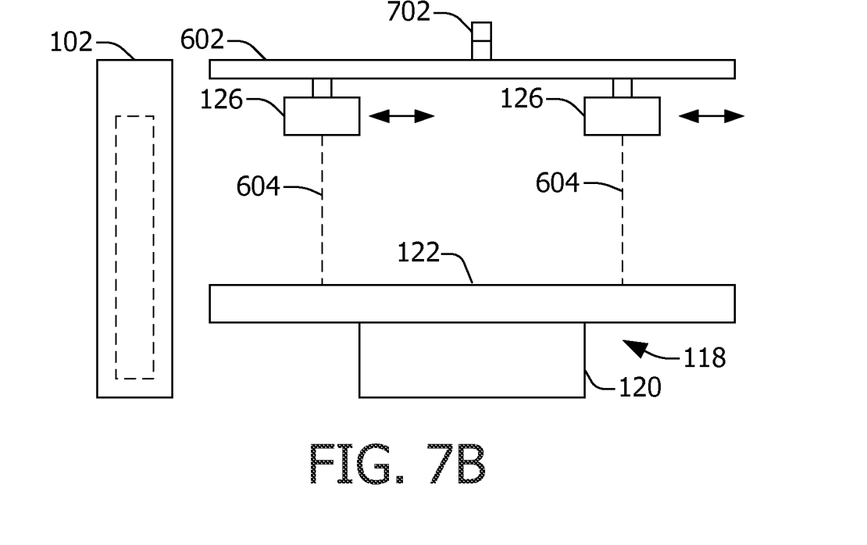

FIG. 7 illustrates an embodiment in which the tracts 602 are fixed to a structure such as an arm 702, which may be mounted to the stationary gantry 102 or other structure separate from the system 100, such as a portable apparatus with wheels, a wall in the exam room, etc.

Figure 8:
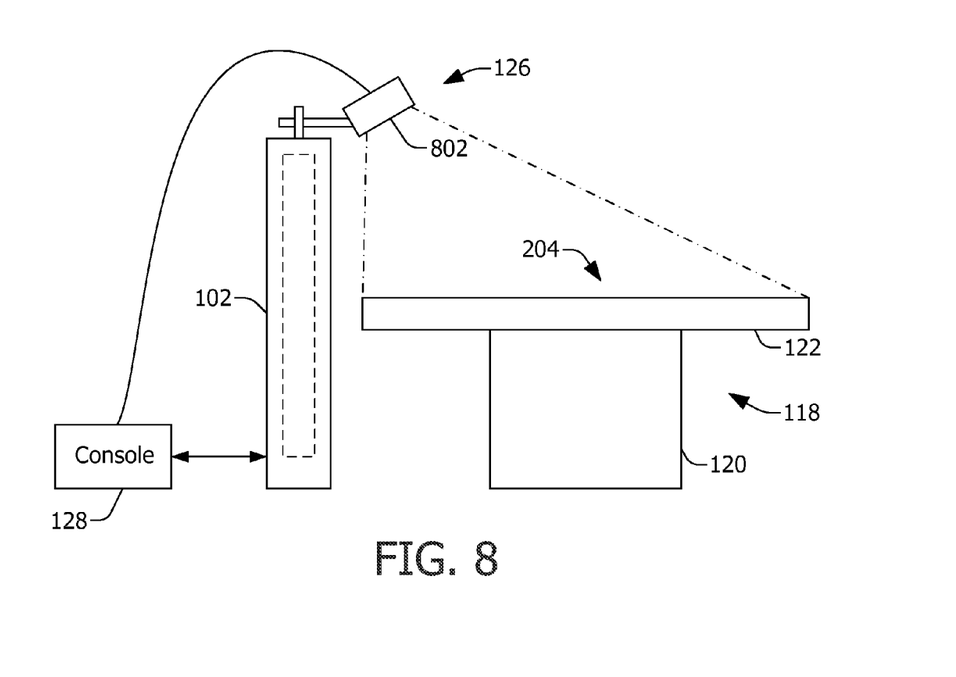

FIG. 8 illustrates an example embodiment in which the scan position identifier 126 includes an image sensor 802, such as a camera, a video recorder or the like, affixed to the stationary gantry 102 directly or through one or more members (as shown). In another embodiment, the scan position identifier 126 is affixed to an apparatus other than the stationary gantry 102. The image sensor 802 is configured to sense information (e.g., a picture and/or video) about the surface 204 of the moveable portion 122 such as information about a subject on the surface 204. The illustrated scan position identifier 126 can sense the entire area of the moveable portion 122. In other embodiments, coverage area is greater or less. Furthermore, the scan position identifier 126 may be moveably attached so that the scan position identifier 126 can tilted, rotated, pivoted, and/or otherwise moved to cover a region of interest.

The sensed information is provided to the console 128 or other computing device and can be registered with the subject support 118, incorporated into executing scan planning software, and displayed via a monitor or the like in connection with a scan planning user interface. The operator can interact with the executing scan planning software to identify a start scan position and optionally an end scan position or scan extent based on the displayed information. The operator may also interact with the executing scan planning to change and/or cancel identified start and/or end scan positions. This embodiment may mitigate a possibility of the subject on the surface 204 of the subject support 118 interacting with the scan position identifier 126. In another embodiment, the scan position identifier 126 may alternatively be affixed to the subject support 118. In another embodiment, more than one scan position identifier 126 is utilized.

Figure 9:
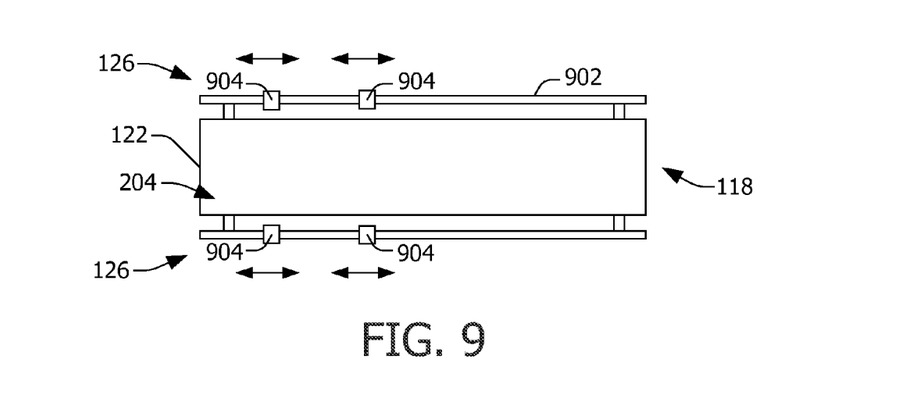

FIG. 9 illustrates an example embodiment in which the scan position identifier 126 includes a rail 902 and one or more members 904 slideably affixed to the rail 902. The one or more members 904 can be used to identify a start scan and optionally an end position. For example, in one embodiment, a technologist slides the members 904 along the rail 902 until the members 904 align with desired scan start and end positions. A signal indicative of the start position (and end position, if one is identified) is generated, and initiating the scan will automatically use the start position (and end position) based on the signal. Where an end position is not identified, the scan extent can be automatically determined, for example, based on selected protocol or otherwise, or manually defined by the technician at the console. An example of suitable members 904 includes, but is not limited to, position-detectable ring, bead, or the like.

In FIGS. 6-9, similar to FIG. 2-5, the scan position identifier 126 is shown on both sides of the subject support 118 and allows for identifying both start and end positions. In another embodiment, the scan position identifier 126 is located on only one side of the subject support 118. Additionally or alternatively, the scan position identifier 126 only allows for identifying one or the start or end positions. An extent can then be determined for the identified start or end position, which facilitates determining the start position or end position. In another embodiment, the scan position identifier 126 is located on both sides, and one side is used to identify the start position while the other side is used to identify the end position.

Figure 10:
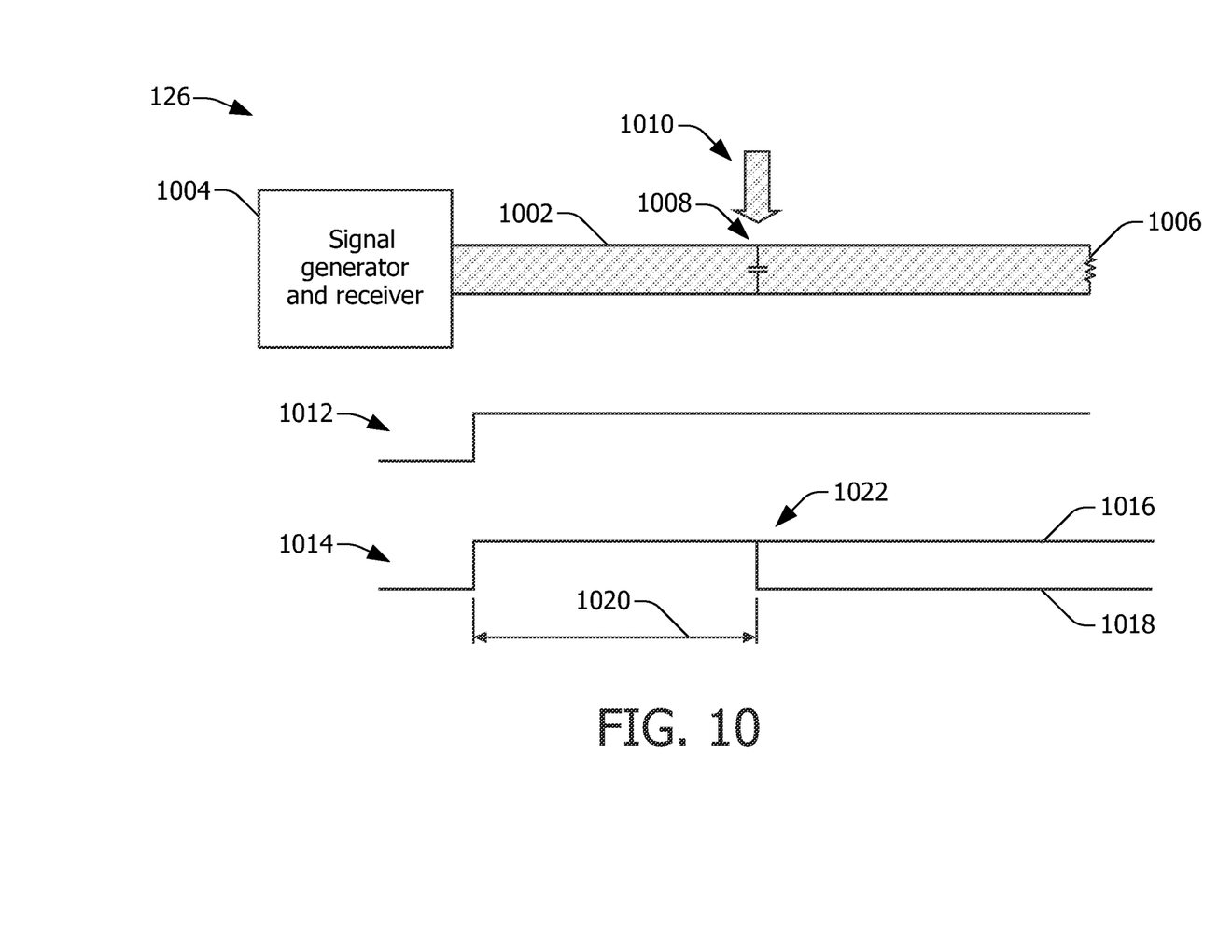
FIG. 10 illustrates a non-limiting example implementation of the scan position identifier.

As briefly discussed above, various approaches can be used to implement the scan position identifier 126. For sake of brevity and explanatory purposes, FIG. 10 illustrates an embodiment utilizing a non-limiting capacitive approach. More particularly, in FIG. 10, the scan position identifier 126 includes a capacitive tape 1002 transmission line or the like. In the illustrated embodiment, one end region of the tape 1002 is in electrical communication with a signal generator and receiver 1004 and another end region of the tape 1002 is electrically terminated via an impedance component 1006.

With this embodiment, a position 1008 is sensed by a transmission line reflection when pressure 1010 is applied to the capacitive tape 1002, which, in this example, causes a change in impedance which causes a reflection, and the reflection is used to calculate the position. An example of this is shown through signals 1012 and 1014. The signal 1012 represents the signal seen by the signal generator and receiver 1004 when the tape 1002 is not being touched. In this example, the signal is a "high" signal. In another embodiment, a "low" or other signal may represent this state. The signal 1014 shows a transition 1022 in the signal, from high 1016 to low 1018 when pressure 1010 is applied to the tape 1002. The reflected wave return time 1020 corresponds to the location of the touch 1010 on the tape 1002 and coincides with the transition, and is used to indentify the position 1008.

A signal indicative of the position 1008 is sent to a console and incorporated with an executing scanning application to mark the start or end scan position along the length of the subject support 118. The scan position is indicated to the operator at the console 128, at a touch panel of the stationary gantry 102, audibly, etc. A scan direction can be determined by the order of the touch positions. A scan length can be adjusted by touching close to one of the previous selected positions ten sliding the finger along the length. The position would be highlighted then moved on the graphic display in real time as the finger moved. An alternate positions sense would be an array of tape switches situated linearly along the length of the couch that could use the same position selecting methods as above.

Other suitable components include, but are not limited to, piezoelectric, magnetic, optical, RF, mechanical, electrical, and/or other components.

Figure 11:
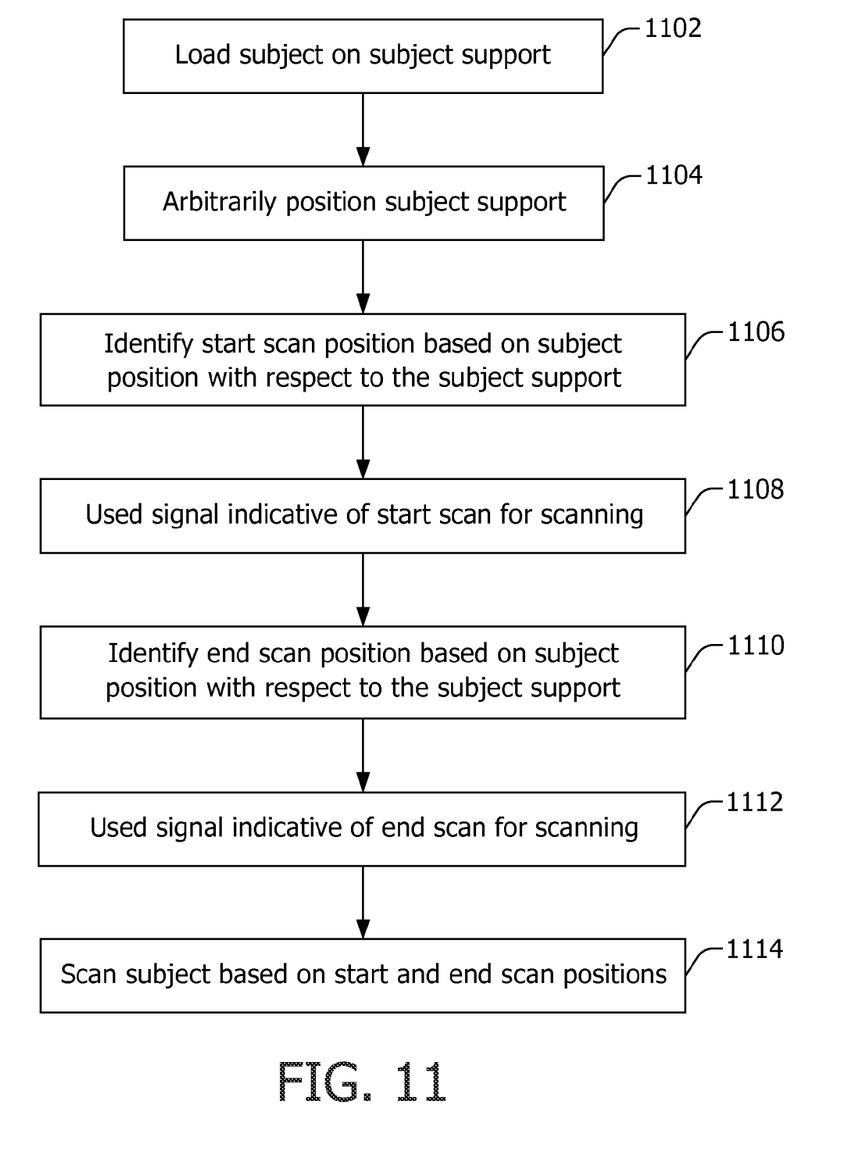
FIG. 11 illustrates a method for identifying at least one of a scan start or end position using the scan position identifier.

FIG. 11 illustrates an example method. It is to be appreciated that the order of the below acts is not limiting. As such, one or more acts may occur in a different order, including concurrently with one or more acts. Furthermore, one or more the acts may be omitted, and/or one or more additional acts may be included.

At 1102, a subject is loaded on the moveable portion 122 of the subject support 118.

At 1104, the technician can move the moveable portion 122 to an arbitrary location with respect to the examination region 106. In another embodiment, the technician may leave the moveable portion 122 where it is.

At 1106, the technician identifies a start scan position by placing or aligning a start scan marker to the subject via the scan position identifier 126 as described herein.

At 1108, a signal indicative of the start position is generated and conveyed to the console or other apparatus used for planning and/or initiating scanning At 1110, optionally, the technician identifies an end scan position by placing or aligning an end scan marker to the subject via the scan position identifier 126 as described herein.

At 1112, if an end position is identified, a signal indicative of the end position is generated and conveyed to the console or other apparatus used for planning and/or initiating scanning At 1114, a scan is initiated utilizing at least the signal indicative of the start scan position. Where an end scan position it identified, the corresponding signal can be used to set the end scan position. Alternatively, a scan extent can be identified, automatically or manually via the technician.

As described herein, in one embodiment, the start and/or end positions and/or can extent may be confirmed or verified or validated by the technician. Furthermore, the start position, the end position, and/or scan extent can be changed, cancelled, etc. Moreover, a visual and/or audible notification (e.g., a warning) may be presented or provided if the scan extent is too large or too small, for example, based on a comparison with a scan extent threshold for a given protocol. In addition, a visual and/or audible notification may be presented or provided if there are any changes in the start/stop position, including the changes. Furthermore, the start and/or end position may be locked at the console or upon start of the scan, which may ensure that they are not changed or reset during the scan.

In the above embodiments, the scan position identifier 126 is described in connection with a CT scanner. However, it is to be appreciated that the scan position identifier 126 can be used with other imaging modalities such as PET, SPECT, MRI, US, multi-modality scanners, imaging systems where a subject patient is placed on a movable subject support that translates into the an examination region for scanning, and/or other imaging system.

It is to be appreciated that the subject support 118 can also be utilized for other applications, including, but not limited to, off-magnet patient scan positioning in connection with an MRI imaging system. An example of suitable off-magnet patient scan positioning is described in application Ser. No. 11/914,951, filed on Nov. 20, 2007, and entitled "Off-Magnet Patient Scan Positioning," which is incorporated herein by reference in its entirety.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

What is claimed is:

1. A subject support that supports a subject to be scanned by an imaging system, comprising:
   a moveable portion that includes a surface on which the subject is loaded and that is configured to move into an examination region of the imaging system where the subject is to be scanned; and
   a scan position identifier that generates a signal indicative of at least one of a start scan position or an end scan position for a predetermined region of interest of the subject based on a location of the region of interest on the moveable portion of the subject support for an arbitrary relative position of the moveable portion with respect to the examination region;
   wherein the scan position identifier includes a capacitive tape transmission line.

2. The subject support of claim 1, wherein the scan position identifier generates the signal independent of the position of the moveable portion with respect to the examination region.

3. The subject support of claim 1, wherein the scan position identifier provides a moveable position marker that is moved to the subject to identify the at least one of the start scan position or the end scan position.

4. The subject support of claim 1, wherein the signal sets at least one of an initial scan start position or an initial end scan position for at least one of a pre-scan or a diagnostic scans.

5. The subject support of claim 1, wherein scan position identifier is affixed to the moveable portion.

6. The subject support of claim 1, further comprising:
   a stationary portion, wherein the moveable portion is slidably affixed to the stationary portion, and wherein the scan position identifier is affixed to the stationary portion.

7. The subject support of claim 1, wherein scan position identifier is located external to the subject support.

8. The subject support of claim 1, wherein scan position identifier includes an image sensor that senses a still picture or video of the position of subject with respect to the moveable portion.

9. The subject support of claim 8, wherein the at least one of the start scan position or the end scan position is identified through the still picture or video.

10. The subject support of claim 1, wherein the scan position identifier includes a touch-sensitive material that generates a signal indicative of a touch corresponding to the at least one of the scan start or scan end positions.

11. The subject support of claim 10, wherein touching the touch-sensitive material to identify the at least one of the scan start or scan end positions causes a change in an electrical characteristic of the touch-sensitive materials, and the signal is indicative of the change in the electrical characteristic.

12. The subject support of claim 11, wherein the electrical characteristic includes at least one of an impedance, a capacitance, a resistance, a voltage or a current.

13. The subject support of claim 11, wherein the at least one of the scan start or scan end positions is determined based on a change in state of the signal.

14. The subject support of claim 1, wherein the scan position identifier includes a feedback component that provides at least one of visual, audible, or tactile feedback corresponding to the at least one of the scan start or scan end positions.

15. A method, comprising:
   generating, with a capacitive tape transmission line, a first signal indicative of one of a start scan position or an end scan position by actuating a portion of the tape aligned with a first region of interest of a subject loaded on a moveable portion of a subject support independent of a location of the moveable portion with respect to an examination region in which the region of interest is scanned; and
   creating a scan plan with at least one of a scan start or end position based on the first signal.

16. The method of claim 15, further comprising:
   generating, with the capacitive tape transmission line, a second signal indicative of the other of the start scan position or the end scan position by actuating a portion of the tape aligned with a second region of the tissue of interest independent of the location of the moveable portion with respect to the examination region in which the region of interest is scanned; and
   creating the scan plan with the scan start and end positions based on the first and second signals.

17. The method of claim 15, further comprising:
   visually illuminating the one of the start scan position or the end scan position.

18. An imaging system, comprising:
   a stationary gantry;
   a rotating gantry, including: a radiation source that emits radiation and a radiation sensitive detector array located opposite the source across an examination region;
   a subject support that supports a subject for scanning and is configured to move the subject into and out of the examination region; and
   a scan position identifier that includes a capacitive tape and identifies at least a start scan position for the subject on the subject support.

* * * * *